(12) United States Patent
Spitz et al.

(10) Patent No.: US 9,127,303 B2
(45) Date of Patent: Sep. 8, 2015

(54) METHOD FOR DETECTION OF BETA-D-GLUCURONIDASE ACTIVITY IN A SAMPLE

(75) Inventors: Urs Spitz, Herrliberg (CH); Lukas Wick, Winterthur (CH); Gunter Schabert, Goldach (CH)

(73) Assignee: Biosynth AG (CH)

( * ) Notice: Subject to any disclaimer, the term of this patent is extended or adjusted under 35 U.S.C. 154(b) by 0 days.

(21) Appl. No.: 14/123,861

(22) PCT Filed: Jun. 8, 2012

(86) PCT No.: PCT/EP2012/060870
§ 371 (c)(1),
(2), (4) Date: Dec. 4, 2013

(87) PCT Pub. No.: WO2012/168415
PCT Pub. Date: Dec. 13, 2012

(65) Prior Publication Data
US 2014/0212905 A1    Jul. 31, 2014

(30) Foreign Application Priority Data
Jun. 8, 2011 (EP) .................................. 11169147

(51) Int. Cl.
*C12Q 1/44* (2006.01)
*C12Q 1/34* (2006.01)
*C12Q 1/04* (2006.01)
*C12Q 1/06* (2006.01)
*C12Q 1/10* (2006.01)

(52) U.S. Cl.
CPC .. *C12Q 1/34* (2013.01); *C12Q 1/04* (2013.01); *C12Q 1/06* (2013.01); *C12Q 1/10* (2013.01)

(58) Field of Classification Search
USPC ............................. 435/19, 18; 536/4.1, 18.5
See application file for complete search history.

(56) References Cited

U.S. PATENT DOCUMENTS

| | | | | |
|---|---|---|---|---|
| 4,518,691 | A | * | 5/1985 | Herlihy ............................ 435/74 |
| 5,268,463 | A | | 12/1993 | Jefferson |
| 5,358,854 | A | | 10/1994 | Ferguson |
| 5,599,670 | A | | 2/1997 | Jefferson |
| 5,633,144 | A | | 5/1997 | Bitton et al. |
| 5,846,761 | A | * | 12/1998 | Rambach ......................... 435/34 |
| 6,534,637 | B2 | | 3/2003 | Shen et al. |

FOREIGN PATENT DOCUMENTS

EP    0 025 467 B1    3/1981

OTHER PUBLICATIONS

D. Zhenjun et al., "Fluorescent molecular probes I. The synthesis and biological properties of an ELF B-glucuronidase substrates that yields fluorescent precipitates at the enzymatic activity sites", Tetrahedron, May 26, 1997, vol. 53, No. 21, 7159-7164.

X. Wu et al., "Sensitive method for the quantification of β-glucuronidase activity in human urine using capillary electrophoresis with fluorescence detection", Journal of Chromatography B: Biomedical Sciences & Applications, Apr. 24, 1998, vol. 708, No. 1-2, pp. 61-66.

J.R. Geary et al., "Hydrolysis of the soluble fluorescent molecule carboxyumbelliferyl-beta-D-glucuronid by *E. coli* beta-glucuronidase as applied in a rugged, in situ optical sensor", Enzyme and Microbial Technology, Jun. 2011, vol. 49, No. 1, pp. 6-10.

T. Garcia-Armisen et al., "β-glucuronidase activity assay to assess viable *Escherichia coli* abundance in freshwaters", Letters in Applied Microbiology, Apr. 1, 2005, vol. 40, No. 4, pp. 278-282.

Manafi et al., "Fluorogenic and chromogenic substrates used in bacterial diagnostics", Microbiol. Rev. 1991, vol. 55, pp. 335-348.

* cited by examiner

*Primary Examiner* — Ralph Gitomer
(74) *Attorney, Agent, or Firm* — George Pappas

(57) ABSTRACT

A method for detection of beta-D-glucuronidase activity in a sample that comprises the steps of (i) providing a glucuronic acid ester compound of the general formula (I) wherein R1 is a C1-4 alkyl group, OR2 is a dye moiety, which is liberated after cleavage of the glycosidic bond; (ii) contacting said glucuronic acid ester compound with a material of said sample exhibiting hydrolytic activity towards glucuronic acid esters, thereby removing R1 and thus forming a sample containing an indicator compound suitable for the detection and/or measurement of beta-D-glucuronidase activity, and (iii) using said indicator to perform an assay requiring detection or measurement of beta-D-glucuronidase activity.

(I)

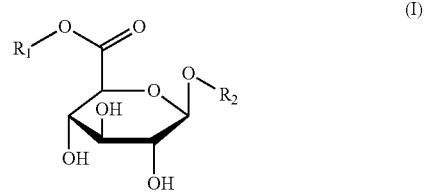

7 Claims, 2 Drawing Sheets

METHOD FOR DETECTION OF BETA-D-GLUCURONIDASE ACTIVITY IN A SAMPLE

This application claims priority from PCT application No. PCT/EP2012/060870 filed Jun. 8, 2012 which claims priory from European application No. EP 11169147.3 filed on Jun. 8, 2011, the disclosures of which are incorporated herein by reference.

FIELD OF THE INVENTION

The present invention discloses a novel method for detection of beta-D-glucuronidase, a key biomarker enzyme. The method is based on the discovery that the most effective glucuronidase indicators can be generated in situ from readily available chemical precursors even if such indicators are not economically accessible by chemical synthesis. This discovery is highly relevant in the context of more rapid and sensitive detection and enumeration of E. coli bacteria commonly used in the microbial assessment of water, food, feed and the environment.

BACKGROUND OF THE INVENTION

The enzyme beta-D-glucuronidase catalyzes the hydrolysis of the O-glycosyl bond in beta-D-glucuronosides with the release of D-glucuronic acid. The enzyme is found in most vertebrates and many molluscs, but generally absent in higher plants, mosses, algae, ferns, fungi, as well as in most bacteria (U.S. Pat. No. 5,268,463).

The beta-D-glucuronidase is often used as a reporter for monitoring promoter activity (GUS reporter system) (U.S. Pat. No. 5,268,463). Indicators for detection of beta-D-glucuronidase consist of a dye molecule conjugated to glucuronic acid through a glycosidic bond, which can be cleaved by beta-D-glucuronidase. Cleavage liberates the dye which then unfolds its characteristic optical properties detectable by eye or suitable equipment. Common indicators in GUS reporter assays are X-beta-D-glucuronic acid, p-nitrophenyl-beta-D-glucuronic acid (PNPGluc) and 4-methylumbelliferyl-beta-D-glucuronide (MUG). However, the spectral properties of these indicators are not ideal. The yellow colour of p-nitrophenol, the cleavage product of PNPGluc, can be difficult to detect in a background with similar coloration, especially in plant tissues. Also, the blue fluorescence of 4-methylumbelliferone, the cleavage product of MUG, is often difficult to distinguish from natural matrix fluorescence (U.S. Pat. No. 5,268,463; U.S. Pat. No. 5,599,670).

Most importantly, beta-D-glucuronidase is a reliable marker for the presence and viability of Escherichia coli bacteria, therefore, providing the basis for common E. coli testing. Such test is typically conducted by contacting a suitable indicator substance sensitive to glucuronidase with a sample and observing the emergence of a signal associated with activity of glucuronidase. A popular fluorogenic indicator (an indicator producing fluorescence upon enzymatic transformation) for such use is MUG. Glucuronidase accepts this substance as a substrate and cleaves it hydrolytically—a process which is evident by the appearance of blue fluorescence.

In bacterial cultures the blue fluorescence of 4-methylumbelliferone is sometimes difficult to distinguish from natural matrix fluorescence or fluorescence from certain Pseudomonas strains (Manafi et al. (1991), Microbiol. Rev. vol. 55, pp. 335-348)). Superior both fluorogenic (e.g. fluorescein-, Resorufin-beta-D-glucuronic acid) and chromogenic (e.g. phenolphthalein-, sulfophenolphthalein-, Resorufin-beta-D-glucuronic acid) indicators are well known in the art but not commonly used due to their prohibitively high cost of manufacturing (U.S. Pat. No. 5,268,463; U.S. Pat. No. 5,599,670; U.S. Pat. No. 6,534,637).

Considering the relative simplicity of such molecules (beta-D-glucuronic acid glycosides) and the rapid advancement of synthetic organic chemistry over the past decades it is surprising that this problem has not yet been resolved. The key of the synthetic challenge is not associated with the formation of the glycosidic linkage between the dye and glucuronic acid as one might expect. It is the subsequent deprotection step of the glucuronic acid moiety of the indicator which causes the problem: For the course of synthesis the non-anomeric hydroxyl groups of glucuronic acid are chemically deactivated by acetylation and the carboxyl group is masked as an ester group. While the former can be removed with ease after glycosidation, cleavage of the glucuronic acid ester often leads to decomposition, rearrangement or lactonization of the indicator molecule. Until today, the lack of much needed sensitive and efficient indicators for glucuronidase is due to this one simple synthetic chemistry problem. Here we do not disclose the long-sought chemical solution to the problem but we describe our discovery that no such solution is needed.

SUMMARY OF THE INVENTION

Here we disclose a novel method for detection of beta-D-glucuronidase activity. The method uses indicators which are made of glycosides of glucuronic acid esters rather than the currently used glycosides of glucuronic acid. We have discovered that glucuronic acid esters linked to dye molecules work as indicators with efficiency comparable to the corresponding indicators derived of glucuronic acid. In the following we demonstrate that glucuronic acid esters are spontaneously hydrolyzed in biological matrices without accompanying decomposition, rearrangement or lactonization often rendering the chemical process useless. Therefore, the bulk manufacturing of glucuronic acid ester derived indicators for certain types of indicators such as indicators releasing Resorufin or Chlorophenol red dyes is by a factor of 50-100 lower in cost compared to their free acid analogues. Due to this massive cost saving indicators of such type can now, based on the discovery disclosed here, be used in common testing.

Surprisingly, we observed that the in situ production of beta-D-glucuronic acid glycosides from the corresponding beta-D-glucuronic acid esters can occur under rather mild and also unexpected conditions in various ways. In one embodiment, it can be non-enzymatic such as by the hydrolytic activity of the buffered media. In a second embodiment, ester hydrolysis and, hence, activation of the indicator is due to esterase activity present in the sample. In a third embodiment, an esterase enzyme is added to the sample in order to accelerate the in situ formation of the indicator. It should be noted that by our account such ester hydrolysis is necessary since glycosides of glucuronic acid esters per se will not efficiently function as substrates for beta-D-glucuronidase but need to be converted to the corresponding glucuronic acids first. For said purpose, glucuronic acids esterified by C1-C4 aliphatic alcohols are best chosen because C1-4 esterase activity is common in most metabolically active prokaryotic and eukaryotic cells. Glucuronic acid ester based indicators can be used in various assays for detection of glucuronidase activity. Many current assays based on glucuronic acid compounds can readily be adapted to assays based on glucuronic acid ester compounds.

BRIEF DESCRIPTION OF THE DRAWINGS

The above mentioned and other features and objects of this invention and the manner of achieving them will become more apparent and this invention itself will be better understood by reference to the following description of various embodiments of this invention taken in conjunction with the accompanying drawings, wherein.

DETAILED DESCRIPTION OF THE INVENTION

During synthesis of indicators for beta-D-glucuronidase, the acid group of the glucuronic acid is protected as an ester group (normally a methyl ester), and the alcohol groups are protected with acetyl groups, which have to be removed in the last steps of synthesis. Removal of the acetyl protecting groups can be achieved by relatively mild conditions with a good yield of product. However, hydrolysis of the methyl ester has to be done under more harsh conditions. The yield in this step is low due to side reactions and decomposition, especially cleavage of the glycosidic linkage. For example, the yield of Chlorophenol red beta-D-glucuronic acid in the last deprotection step was reported to be only about 5% (U.S. Pat. No. 6,534,637). Such low yields increase the costs of the final product considerably, which limits their use drastically.

Figure 1:
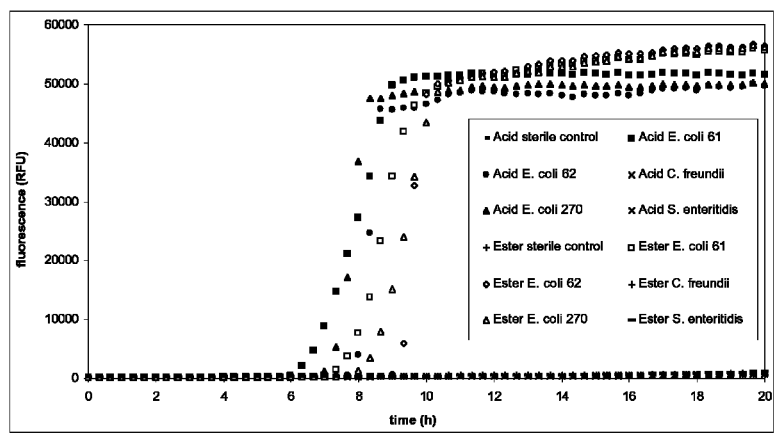
FIG. 1 shows the time course of fluorescence of cultures of *Escherichia coli* (3 strains), *Citrobacter freundii*, *Salmonella enteritidis* and sterile control in a medium containing Resorufin-beta-D-glucuronic acid ("Acid") or Resorufin-beta-D-glucuronic acid methyl ester ("Ester"); cultures were grown in microtiter plates at 37° C. in a Spectramax M5 platereader ($\lambda_{ex}$=570 nm, $\lambda_{em}$=600 nm). Fluorescence in arbitrary units (RFU, relative fluorescence units) is plotted vs. time (h).

This invention discloses a new method for detection of beta-D-glucuronidase activity at lower costs. The basis of the invention is the discovery that the methyl ester of Resorufin-beta-D-glucuronic acid can be used for detection of beta-D-glucuronidase activity in *Escherichia coli* cultures in the same way as the Resorufin-beta-D-glucuronic acid itself (FIG. 1, Table 1).

As described above, indicators based on the glucuronic acid ester can be produced at lower costs making present applications less expensive and even enabling new applications that were too costly to be implemented with the glucuronic acid based indicators.

In the present invention the beta-D-glucuronic acid based indicator is produced in situ from the ester of the beta-D-glucuronic acid compound. The hydrolysis of the ester can be achieved by the activity of a C1-4 esterase, hydroxyl ions or other factors known to hydrolyze such ester compounds. These factors can be inherent in the sample matrix or can be added to the sample matrix. Depending on the type of the assay and sample matrix the hydrolysis conditions have to be selected so that they do not interfere with the assay as a whole.

In preferred embodiments the method is used with matrices that already exhibit an ester hydrolysing activity itself, e.g. as in an enrichment broth for *E. coli*. In further embodiments the ester hydrolyzing activity is conferred to the matrix in an extra step, e.g. by addition of a C1-4 esterase.

Depending on the application, indicator moieties for the beta-D-glucuronic acid ester based indicators can be chosen from the following list:
Resorufin; 7-hydroxycoumarin; 7-hydroxy-4-methylcoumarin; 7-hydroxy-coumarin-3-carboxylic acid; 7-methoxycoumarin; 7-hydroxy-3-acetylcoumarin; 7-hydroxy-4-trifluoromethylcoumarin; 7-hydroxycoumarin-4-acetic acid; 7-hydroxy-3-ethoxycarbonylcoumarin; 6-chloro-7-hydroxy-4-methylcoumarin; 3-cyano-7-hydroxycoumarin; 3-chloro-7-hydroxy-4-methylcoumarin; Alizarin; fluorescein; fluorescein beta-D-glucuronide; 6-Chloro-2-(5-chloro-2-hydroxyphenyl)-4(1H)-quinazolinone (ELF® 97); phenolphthalein; phenolsulfonphthalein; 3',3'-Dichlorophenolsulfonaphthalein (Chlorophenol red); o-nitrophenyl; p-nitrophenyl; m-nitrophenyl; o-chloro-p-nitrophenyl; 1-naphthyl; 2-naphthyl; 6-Brom-2-naphthyl; naphthol-AS-BI; 1-pyrenyl; 2-aminophenyl; 4-aminophenyl; 2-methoxy-4-(2-nitrovinyl)phenyl; 3-indoxyl; 5-bromo-4-chloro-3-indoxyl; 5-bromo-6-chloro-3-indoxyl; 6-chloro-3-indoxyl; 5-bromo-3-indoxyl; 6-fluoro-3-indoxyl; 5-iodo-3-indoxyl; 1-methyl-3-indoxyl; 4-chloro-3-indoxyl; 5-nitro-3-indoxyl; 6-carboxy-3-indoxyl; 5-cyano-4-chloro-3-indoxyl; 5-cyano-3-indoxyl; 8-hydroxyquinoline; 3,4-cyclohexenoesculetin.

Because the ability to induce beta-D-glucuronidase varies among different substrates and conditions, an inducer such as 1-O-methyl-beta-D-glucuronic acid can be added to the assay to increase beta-D-glucuronidase activity.

In a preferred embodiment of the invention the methyl ester of Resorufin-beta-D-glucuronide is added to broth for enrichment of *E. coli*. The broth is inoculated with the sample to be tested and incubated. The presence of *E. coli* in the sample can then be monitored by observing a change in colour of the broth from yellow to pink or by measuring fluorescence emission at 600 nm with excitation at 570 nm. These measurements can be done at the end of the incubation or with adequate equipment as kinetic measurements during the incubation. The pH of the broth should be 7 or higher for optimal detection of the liberated Resorufin.

In a further embodiment of the invention an esterase is added to an assay, if the sample matrix to be tested does not exhibit an ester hydrolysing activity. Assay conditions and the time point of esterase addition have to be chosen so that the ester is hydrolyzed before the beta-D-glucuronidase cleaves the indicator moiety off the beta-D-glucuronic acid.

Since C1-4 esterase activity is common in most metabolically active prokaryotic and eukaryotic cells, beta-D-glucuronic acid ester based indicators can be used in various assays for detection of beta-D-glucuronidase activity. Those skilled in the art can adapt many current assays using beta-D-glucuronic acid based indicators to assays using beta-D-glucuronic acid ester based indicators.

EXAMPLES

Example 1

Detection of Microbial beta-D-glucuronidase in Broth Cultures in Test Tubes

Resorufin-beta-D-glucuronic acid or Resorufin-beta-D-glucuronic acid methyl ester was added to test tubes containing 3 ml of Nutrient Broth (NB: 5 g/l peptone, 5 g/l NaCl, 2 g/l yeast extract, 1 g/l beef extract, pH 7.4) or Tryptone Bile Broth (TBB: 20 g/l tryptone, 1.5 g/l bile salts No. 3) at a concentration of 0.1 mM. Tubes were inoculated with cultures pregrown over night on NB and incubated at 37° C. for 16 hours. Tubes were scored visually for beta-D-glucuronidase activity as positive (pink colour) or negative (yellow colour). Both substrates gave the same results for all strains tested (Table 1), showing that the Resorufin-beta-D-glucuronic acid methyl ester can be used in place of the Resorufin-beta-D-glucuronic acid for detection of E. coli.

TABLE 1

Determination of beta-D-glucuronidase activity of various species tested with either Resorufin-beta-D-glucuronic acid or Resorufin-beta-D-glucuronic acid methyl ester in broth cultures.

| Species | Number of strains tested | Tested in | Result of Resorufin-beta-D-glucuronic acid | Result of Resorufin-beta-D-glucuronic acid methyl ester |
|---|---|---|---|---|
| Acinetobacter baumanii | 1 | NB | negative | negative |
| Aeromonas hydrophila | 1 | TBB | negative | negative |
| Bacillus cereus | 1 | NB | negative | negative |
| Citrobacter freundii | 1 | TBB | negative | negative |
| Enterobacter aerogenes | 1 | NB | negative | negative |
| Enterobacter cloacae | 1 | NB | negative | negative |
| Enterococcus faecalis | 1 | TBB | negative | negative |
| Escherichia coli | 19 | TBB | positive | positive |
| Escherichia coli O157:H7 | 2 | TBB | negative | negative |
| Hafnia alvei | 1 | NB | negative | negative |
| Klebsiella pneumoniae | 1 | TBB | negative | negative |
| Proteus vulgaris | 1 | NB | negative | negative |
| Pseudomonas aeruginosa | 1 | TBB | negative | negative |
| Salmonella Enteritidis | 1 | TBB | negative | negative |
| Salmonella Typhimurium | 1 | NB | negative | negative |
| Serratia marcescens | 1 | TBB | negative | negative |
| Staphylococcus aureus | 1 | NB | negative | negative |
| Staphylococcus haemolyticus | 1 | NB | negative | negative |
| Vibrio parahaemolyticus | 1 | NB | negative | negative |
| Yersinia enterocolitica | 1 | NB | negative | negative |
| Sterile control | | NB, TBB | Negative | negative |

Example 2

Detection of Microbial beta-D-glucuronidase Activity in Broth Cultures in Microtiter Plates Wells of a microtiter plate were filled with Nutrient Broth (NB: 5 g/l peptone, 5 g/l NaCl, 2 g/l yeast extract, 1 g/l beef extract, pH 7.4) containing Resorufin-beta-D-glucuronic acid or Resorufin-beta-D-glucuronic acid methyl ester at concentrations of 0.1 mM. The wells were inoculated with about 10 cfu of cultures pregrown over night on NB and incubated at 37° C. for 20 hours. Fluorescence was measured every 20 minutes at an excitation wavelength of 570 nm and an emission wavelength of 600 nm (FIG. 1). For both substrates an increase in fluorescence with the beta-D-glucuronidase positive strains was measured. The increase in fluorescence in cultures with the Resorufin-beta-D-glucuronic acid methyl ester was a little slower than the increase in fluorescence for the Resorufin-beta-D-glucuronic acid. The negative control and the beta-D-glucuronidase negative strains showed only low background signal for both substrates.

Example 3

Enzymatic Assay with Purified beta-D-glucuronidase

Figure 2:
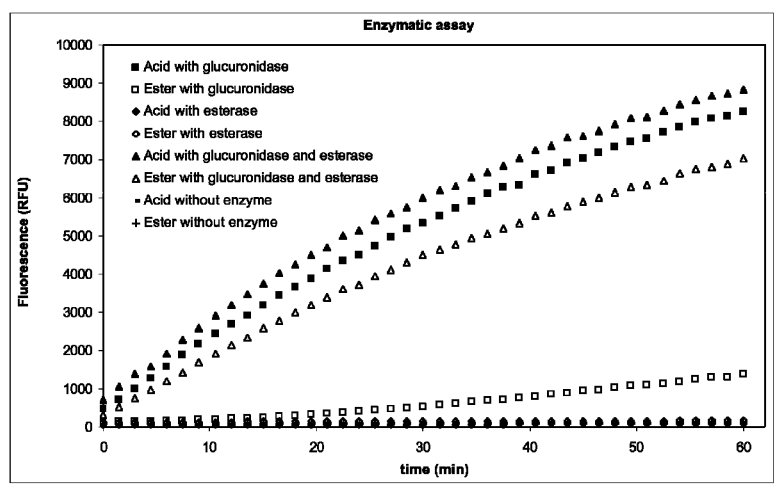
FIG. 2 shows the time course of fluorescence of enzymatic assays. Resorufin-beta-D-glucuronic acid or Resorufin-beta-D-glucuronic acid methyl ester was incubated in presence of glucuronidase, esterase, both enzymes or without enzyme. Measurements were done in microtiter plates at 37° C. in a Spectramax M5 platereader ($\lambda_{ex}$=570 nm, $\lambda_{em}$=600 nm). Fluorescence in arbitrary units (RFU, relative fluorescence units) is plotted vs. time (min).

Wells of a microtiter plate were filled with buffer (35 mM potassium phosphate, 4.7 mg/ml bovine serum albumin, pH 6.8) containing Resorufin-beta-D-glucuronic acid or Resorufin-beta-D-glucuronic acid methyl ester at concentrations of 0.1 mM. To the wells were added either a) 0.3 unit beta-D-glucuronidase (type VII-A from E. coli) or b) 10 units esterase (from porcine liver) or c) 0.3 unit beta-D-glucuronidase and 10 units esterase or d) no enzyme. The microtiter plate was incubated at 37° C. for 1 hour. Fluorescence was measured every 1.5 minutes at an excitation wavelength of 570 nm and an emission wavelength of 600 nm (FIG. 2). Wells with Resorufin-beta-D-glucuronic acid showed a fast increase of fluorescence in the presence of beta-D-glucuronidase independent of the presence of esterase. Wells with Resorufin-beta-D-glucuronic acid methyl ester showed a fast increase of fluorescence in the presence of beta-D-glucuronidase and esterase, and only a slow increase of fluorescence in the presence of beta-D-glucuronidase without esterase. The negative control and the wells with esterase only showed low background signal for both substrates.

Example 4

Detection of Microbial beta-D-glucuronidase in Preincubated Medium

Figure 3:
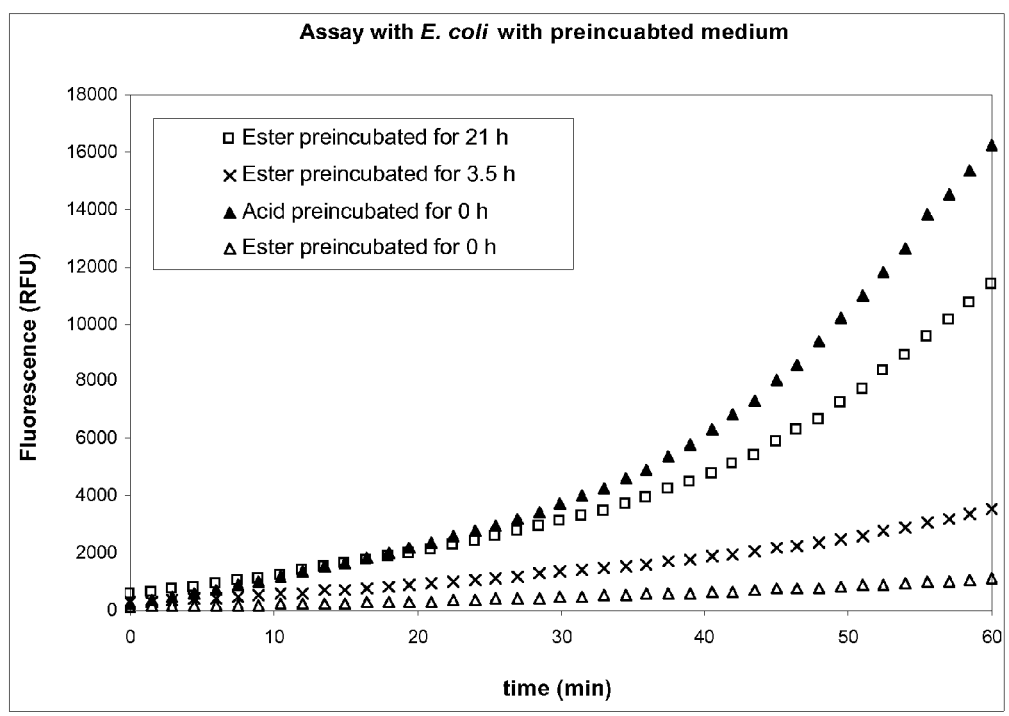
FIG. 3 shows the time course of fluorescence of an *E. coli* culture mixed with media containing Resorufin-beta-D-glucuronic acid or Resorufin-beta-D-glucuronic acid methyl ester. The media with the Resorufin-beta-D-glucuronic acid methyl ester were preincubated for different time periods. Measurements were done in microtiter plates at 37° C. in a Spectramax M5 platereader ($\lambda_{ex}$=570 nm, $\lambda_{em}$=600 nm). Fluorescence in arbitrary units (RFU, relative fluorescence units) is plotted vs. time (min).

Wells of a microtiter plate were filled with 100 μl Nutrient Broth (NB: 5 g/l peptone, 5 g/l NaCl, 2 g/l yeast extract, 1 g/l beef extract, pH 7.4) containing Resorufin-beta-D-glucuronic acid or Resorufin-beta-D-glucuronic acid methyl ester at concentrations of 0.2 mM. The wells were incubated for different times (21 h, 3.5 h, 0 h) at 37° C. After incubation, 100 μl of an E. coli culture pregrown over night on NB was added (about $10^8$ cfu/ml). Fluorescence was measured every 1.5 minutes at an excitation wavelength of 570 nm and an emission wavelength of 600 nm (FIG. 3). The longer the preincubation time of the medium, the more Resorufin-beta-D-glucuronic acid originated from the Resorufin-beta-D-glucuronic acid methyl ester through hydrolysis. The result of this process is that the signal obtained from media originally containing the Resorufin-beta-D-glucuronic acid methyl ester gets closer to the signal from media originally containing the Resorufin-beta-D-glucuronic acid with longer preincubation time. The hydrolysis is surprisingly fast at the medium pH of 7.4.

The invention claimed is:
1. A method for detection of beta-D-glucuronidase activity in a sample, comprising the steps of:
   (i) providing said sample with a material exhibiting hydrolytic activity towards glucuronic acid esters;
   (ii) contacting said sample with an amount of resorufin-beta-D-glucuronic acid methyl ester, whereby said material exhibiting hydrolytic activity towards glucuronic acid esters causes removing a methyl group and thus forming a sample containing an indicator com- pound suitable for the detection and/or measurement of beta-D-glucuronidase activity, and (iii) performing a detection or measurement of beta-D-glucuronidase activity in said sample by means of said indicator compound.

2. The method according to claim 1, wherein performing said detection or measurement is based on a change of colour or fluorescence of said indicator compound.

3. The method according to claim 1, wherein said sample contains prokaryotic or eukaryotic cells, cell extracts, biological liquids, tissues or organisms.

4. The method according to claim 1, wherein said hydrolytic activity is due to chemical and physical properties of buffers or broths processed in the method.

5. The method according to claim 1, wherein said hydrolytic activity is due to enzymatic activity.

6. The method according to claim 1, wherein said hydrolytic activity results from use of a medium for *E. coli* detection or *E. coli* cells.

7. The method according to claim 2, wherein said sample contains prokaryotic or eukaryotic cells, cell extracts, biological liquids, tissues or organisms.

* * * * *